United States Patent [19]

Frei et al.

[11] Patent Number: 4,857,509
[45] Date of Patent: Aug. 15, 1989

[54] 13β-ALKYLMILBEMYCIN DERIVATIVES FOR CONTROLLING PARASITES OF ANIMALS AND PLANTS

[75] Inventors: Bruno Frei, Liestal; Anthony C. O'Sullivan, Basel; Jean-Claude Gehret, Aesch, all of Switzerland

[73] Assignee: CIBA-GEIGY Corporation, Ardsley, N.Y.

[21] Appl. No.: 820,490

[22] Filed: Jan. 17, 1986

[30] Foreign Application Priority Data

Jan. 22, 1985 [CH] Switzerland ............................ 278/85

[51] Int. Cl.⁴ ..................... A61K 31/70; C07M 17/04; C07D 313/06
[52] U.S. Cl. ...................................... 514/30; 514/450; 536/7.1; 549/264; 549/265; 549/268; 71/65; 71/88
[58] Field of Search ...................... 514/30, 450; 71/65, 71/88; 536/7.1; 549/264, 265, 268

[56] References Cited

U.S. PATENT DOCUMENTS 3,950,360 2/1976 Aoki et al. .................... 260/343.2 R
4,173,571 5/1979 Chabala et al. ............... 260/343.41
4,346,171 7/1982 Takiguchi et al. ................... 435/119

FOREIGN PATENT DOCUMENTS 0180539 5/1986 European Pat. Off. ............ 549/264
2167751 6/1986 United Kingdom ................. 536/7.1

Primary Examiner—Johnnie R. Brown
Assistant Examiner—Elli Peselev
Attorney, Agent, or Firm—Edward McC. Roberts; Meredith C. Findlay

[57] ABSTRACT

The invention relates to parasiticidally and insecticidally highly active compounds of formula I

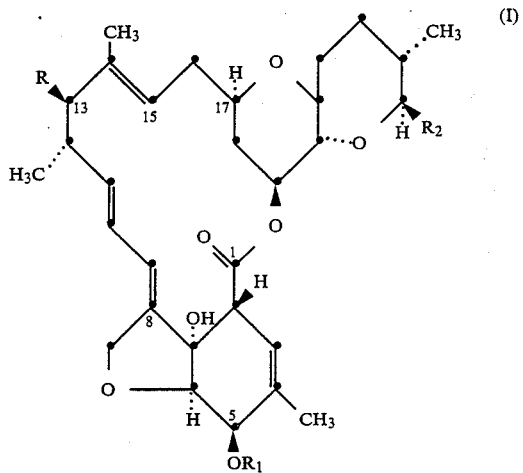

wherein
R is $C_1$–$C_{10}$alkyl;
$R_1$ is hydrogen, a silyl group or a sugar residue; and
$R_2$ is methyl, ethyl, isopropyl or sec-butyl, and to the preparation thereof starting from suitably substituted 15-ester or 13β-ester milbemycins.

18 Claims, No Drawings

13β-ALKYLMILBEMYCIN DERIVATIVES FOR CONTROLLING PARASITES OF ANIMALS AND PLANTS

The present invention relates to novel 13β-alkyl-milbemycin derivatives of formula I below, to the preparation thereof and to the use thereof for controlling pests such as ecto- and endoparasites of animals and parasites of plants.

The compounds of the present invention are 13β-alkylmilbemycins of the general formula I

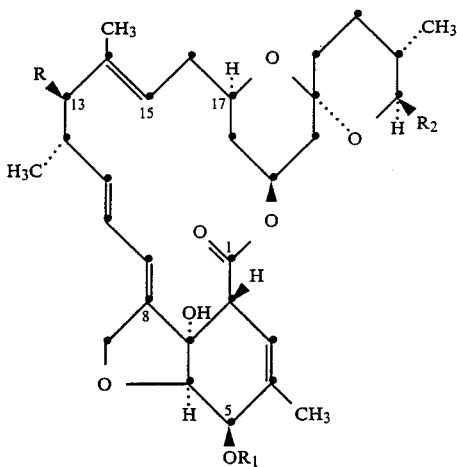

wherein

R is $C_1$-$C_{10}$alkyl;

$R_1$ is hydrogen, a silyl group or a sugar residue; and $R_2$ is methyl, ethyl, isopropyl or sec-butyl.

Thus formula I represents milbemycin derivatives which contain a 13β-alkyl group and which carry in the 5-position a free OH group, a silyl group or a sugar residue, in particular a mono-, di- or trisaccharide which carries in the ortho-position relative to the O—$R_1$ bond an OH group which is in turn preferably derivativised.

Depending on the number of carbon atoms indicated, alkyl by itself or as moiety of another substituent will be understood as meaning for example the following groups: methyl, ethyl, propyl, butyl, pentyl, hexyl, heptyl, octyl, nonyl, decyl, etc., as well as the isomers thereof, e.g. isoopropyl, isobutyl, tert-butyl, isopentyl etc.

Suitable silyl groups $R_1$ are the radicals —Si($R_5$)($R_6$)($R_7$), wherein $R_5$, $R_6$ and $R_7$, preferably independently, are each $C_1$-$C_4$alkyl, benzyl or phenyl and form for example one of the groups trimethylsilyl, tris(tert-butyl)silyl, diphenyl-tert-butylsilyl, bis(isopropyl)methylsilyl, triphenylsilyl etc. and, in particular, tert-butyldimethylsilyl. The 5—OH group may also occur as benzyl ether or methoxyethoxymethyl ether.

Within the scope of the present invention, a sugar residue shall be understood as meaning preferably a carbohydrate group —A—(B)$_k$—(C)$_m$, wherein A is a carbohydrate residue which is bonded in the 1'-position and which carries in the 2'-position either a hydroxy group or a readily removable group bonded through oxygen, and which carbohydrate residue A may be bonded glycosidically to a second and/or third carbohydrate molecule B and/or C of any structure, and each of k and m independently of the other is 0 or 1.

Thus examples of suitable sugar residues substituted in the 2'-position as indicated above are the following residues occurring in the furanosyl form or in the pyranosyl form:

monosaccharides: glucose, fructose, altrose, mannose, sorbose, gulose, idose, allose, galactose, ribose, arabinose, xylose, lyxose, erythrose, threose, thamnose and talose, as well as the corresponding derivatives thereof, such as methyl glucose, trimethyl glucose and tetraacetyl glucose, and also mono- or polyacetylated sugars;

disaccharides: lactose, maltose, cellobiose, melibiose and gentiobiose, as well as the corresponding derivatives thereof.

The carbohydrates indicated for formula I also comprise saccharides which additionally contain an amino radical, a thiol radical or a cyclic acetal radical formed from two adjacent OH groups and an aldehyde or ketone.

The saccharide bonded in the 5-position of the compounds of formula I may be in the form of an α-anomer or β-anomer. The present invention relates to both types of bonding.

Examples of readily removable groups bonded through oxygen in the 2'-position of the sugar residue are methyl, benzyl, an unsubstituted or halogenated $C_1$-$C_6$aliphatic acyl group, a benzoyl group or a $C_1$-$C_6$alkoxycarbonyl group.

In the foregoing definitions, halogen is preferably fluorine, chlorine or bromine.

The following are suitable for the formation of a cyclic acetal bonded to a sugar molecule: simple aldehydes such as acetaldehyde, propionaldehyde, butyraldehyde or benzaldehyde, or ketones such as acetophenone, cyclopentanone, cyclohexanone, cycloheptanone, fluorenone, methyl ethyl ketone and, in particular, acetone with the formation of corresponding acetonides.

Throughout this specification, compounds wherein $R_2$ is sec-butyl will also be considered as belonging to the class of milbemycin derivatives although according to conventional classification they do not belong to this class but, in accordance with U.S. Pat. No. 4,173,571, are derived from avermectin derivatives.

Compounds of formula I wherein $R_1$ is a silyl group or a sugar residue can be converted by simple, e.g. hydrolytic, removal of this function into the highly active free 5-hydroxy derivative ($R_1$=H) and act therefore as intermediates. However, the biological value of these compounds is intrinsically not diminished by the protecting group.

In naturally occurring milbemycins ($R_1$=H; $R_2$=$CH_3$, $C_2H_5$ or iso$C_3H_7$) the substituent R in the 13-position is always hydrogen. However, in avermectins an α-L-oleandrosyl-α-oleandrose radical which is bound through oxygen in the α-configuration to the macrolide molecule is in the 13-position. Moreover, avermectins differ structurally from milbemycins by the presence of a 23-OH group or $\Delta^{22,23}$ double bond and, usually, by the presence of a substituent $R_2$=sec-$C_4H_9$. By hydrolysing the sugar residue of avermectins, the corresponding avermectinaglycons containing an allylic 13α-hydroxyl group are readily obtained. In the avermectin derivatives of the present invention the $\Delta^{22,23}$ double bond always occurs in hydrogenated form.

On account of their pronounced parasiticidal and insecticidal activity, the following subgroups of compounds of formula I are particularly preferred:

Group Ia

Compounds of formula I, wherein R is $C_1$-$C_{10}$alkyl; $R_1$ is the group —Si($R_5$)($R_6$)($R_7$), wherein each of $R_5$, $R_6$ and $R_7$ independently of one another is $C_1$-$C_4$alkyl, benzyl or phenyl; and $R_2$ is methyl, ethyl, isopropyl or sec-butyl.

Group Ib

Those compounds within subgroup Ia, wherein R is $C_1$-$C_4$-alkyl; $R_1$ is trimethylsilyl, tris(tert-butyl)silyl, diphenyl-tert-butylsilyl, bis(isopropyl)methylsilyl, triphenylsilyl or tert-butyldimethylsilyl; and $R_2$ is methyl, ethyl, isopropyl or sec-butyl.

Group Ic

Compounds of formula I, wherein R is $C_1$-$C_{10}$alkyl; $R_1$ is hydrogen, a silyl group or the carbohydrate group —A—(B)$_k$—(C)$_m$), wherein A is carbohydrate residue which is bonded in the 1'-position and which carries in the 2'-position either a hydroxy group or a readily removable group bonded through oxygen, and which carbohydrate residue A may be bonded glycosidically to a second and/or third carbohydrate molecule B and/or C of any structure, and each of k and m independently of the other is 0 or 1; and $R_2$ is methyl, ethyl, isopropyl or sec-butyl.

Group Id

Compounds of formula I, wherein R is $C_1$-$C_{10}$alkyl; $R_1$ is the sugar residue

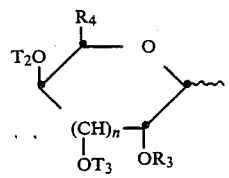

including the position isomers thereof, in which formula n is 0 or 1, $R_4$ is hydrogen, methyl or —$CH_2$—O—$T_1$, and each of $R_3$, $T_1$, $T_2$ and $T_3$ independently of one another is hydrogen, methyl, benzyl an unsubstituted or halogenated $C_1$-$C_6$aliphatic acyl group, a benzoyl group, or a $C_1$-$C_6$alkoxycarbonyl group, or $T_1$ and $T_2$ together with the carbon atom of the carbonyl group of an aliphatic or aromatic aldehyde or ketone form a cyclic acetal containing not more than 13 carbon atoms; and $R_2$ is methyl, ethyl, isopropyl or sec-butyl.

Group Ie

Those compounds within the scope of the subgroup of formula Id, wherein R is $C_1$-$C_4$alkyl; $R_3$ is methyl, benzyl, benzoyl, unsubstituted or fluorinated propionyl, acetyl, methoxycarbonyl or ethoxycarbonyl; and $R_2$, $R_4$, $T_2$ and $T_3$ are as defined for formula Id.

Group If

Compounds of formula I, wherein R is $C_1$-$C_{10}$alkyl; $R_1$ is hydrogen; and $R_2$ is methyl, ethyl, isopropyl or sec-butyl. Compounds of group If are particularly preferred.

Group Ig

Compounds of formula I, wherein R is $C_1$-$C_6$alkyl; $R_1$ is hydrogen; and $R_2$ is methyl, ethyl, isopropyl or sec-butyl.

Group Ih

Compounds of formula I, wherein R is $C_1$-$C_4$alkyl; $R_1$ is hydrogen; and $R_2$ is methyl, ethyl, isopropyl or sec-butyl.

Group Ii

Compounds of formula I, wherein R is methyl, ethyl, n-propyl or isopropyl; $R_1$ is hydrogen; and $R_2$ is methyl, ethyl or isopropyl.

Examples of particularly preferred individual compounds of formula I are:

13$\beta$-n-hexylmilbemycin D,

13$\beta$-methylmilbemycin D,

13$\beta$-ethylmilbemycin D,

13$\beta$-n-propylmilbemycin $A_4$,

13$\beta$-isopropylmilbemycin $A_4$,

13$\beta$-methylmilbemycin $A_3$

13$\beta$-ethylmilbemycin $A_3$

13$\beta$-methylmilbemycin $A_4$

13$\beta$-ethylmilbemycin $A_4$

13$\beta$-isobutylmilbemycin $A_4$

13$\beta$-n-butylmilbemycin $A_4$.

The present invention relates not only to the compounds of formula I but also to the novel process for the preparation thereof. It has been found that the allyl esters of formula II defined below, wherein the allylic $OR_8$ group is in the 15-position of the molecule, can be converted by reaction with trialkylaluminium compounds of the formula Al(R)$_3$ into the compounds of formula I such that the substituent R to be introduced occupies the 13$\beta$-position of the molecule stereospecifically and affords only small amounts of by-products, which are substituted in the 15-position. $R_8$ is acyl, e.g.: formyl, acetyl, benzoyl, ethoxycarbonyl or P(=O)(alkoxy)$_2$ such as P(=O)(OEt)$_2$, alkylsulfonyl, preferably lower alkylsulfonyl, in particular mesyl, and, in certain cases, also tetrahydropyranyl.

It has also been found that compounds of formula II containing a 13$\beta$—$OR_8$ group can, while retaining the 13$\beta$-orientation, be converted into compounds of formula I. The process of the present invention therefore also makes it possible to introduce selectively an alkyl group R into the 13$\beta$-position of milbemycin derivatives or 13-deoxy-22,23-dihydroavermectin derivatives and so to obtain highly effective novel parasiticides and insecticides which may also be used for the formation of further milbemycin derivatives.

Accordingly, the present invention relates to a process for the preparation of compounds of formula I, which process comprises treating an allyl ester of formula II

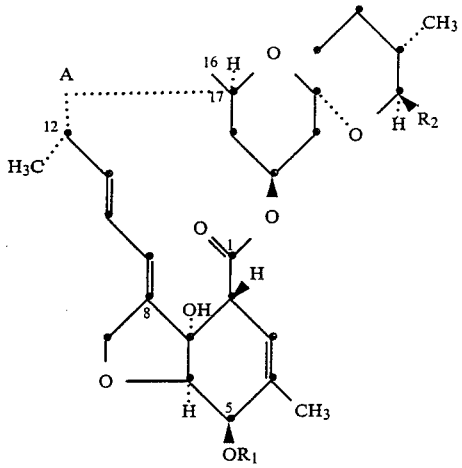

wherein A is one of the groups a or b

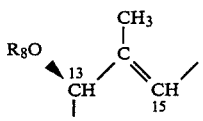

[= 13β-ester-Δ$^{14,15}$]

or

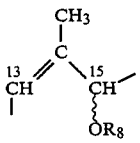

[= Δ$^{13,14}$-15-ester]

$R_8$ is an acyl group, $R_1$ is hydrogen or, preferably, a silyl group, and $R_2$ is as defined for formula I, with a trialkylaluminium compound of formula III $$Al(R)_3 \qquad (III)$$

wherein R is as defined for formula I, and, if free 5-hydroxy compounds are desired, subsequently removing the silyl group $R_1$ by hydrolysis and, to introduce a sugar residue $R_1$, reacting a 5-hydroxy compound of formula I with a sugar derivative suitable for the introduction of said sugar residue.

The process is generally carried out in an inert solvent. Suitable solvents are e.g.: ethers and ethereal compounds such as dialkyl ethers (diethyl ether, diisopropyl ether, tert-butylmethyl ether, dimethoxyethane, dioxane, tetrahydrofuran, anisole etc.); halogenated hydrocarbons such as chlorobenzene, methylene chloride, ethylene chloride, etc.; or sulfoxides such as dimethyl sulfoxide. Aromatic or aliphatic hydrocarbons such as benzene, toluene, xylenes, petroleum ether, ligroin, cyclohexane etc. may also be present. In some cases it may be advantageous to carry out the reaction or partial steps thereof in an inert gas atmosphere (e.g. argon, helium, nitrogen etc.) and/or in absolute solvents. If desired, intermediates may be isolated from the reaction medium and, if desired, be purified in conventional manner before further reaction, e.g. by washing, digesting, extraction, recrystallisation, chromatography etc. However, such reaction steps may be dispensed with and only carried out with the corresponding final products.

Trialkylaluminium compounds suitable for the introduction of the 13β-alkyl group are ($C_1$-$C_{10}$alkyl)-3aluminium compounds such as trimethylaluminium, triethylaluminium, triisobutylaluminium, trihexylaluminium etc. The reaction is generally carried out in the temperature range from −100° C. to +100° C., preferably from −20° C. to +60° C. The trialkylaluminium compound of formula III is added in substance or in an inert solvent, e.g. hexane, toluene or benzene, in at least equimolar amount to the solution of the compound of formula II.

When the reaction is complete, the silyl protecting group is conveniently removed by treating the compound of formula I with a dilute acid, e.g. with 1% p-toluenesulfonic acid in methanol or with an aqueous HF solution in acetonitrile, in the temperature range from −20° C. to +50° C., preferably from 0° C. to +30° C., or with pyridinium fluoride in pyridine.

The preparation of compounds of formula I which carry a carbohydrate residue bonded to the oxygen atom in the 5-position is a derivativisation of the very reactive 5-hydroxy group of the 13β-alkylmilbemycin with a suitable carbohydrate molecule and is carried out in accordance with a bonding method employed in sugar chemistry, e.g. in accordance with Koenigs-Knorr synthesis, the silver triflate process, the orthoester method, phenylthio synthesis or 2-pyridylthio synthesis.

(A) In accordance with Koenigs-Knorr synthesis or the silver triflate process, a 13β-alkylmilbemycin of formula I ($R_1$=OH) can be bonded, in the presence of a silver salt or mercury salt as condensing agent, with the sugar residue to be introduced, the carbohydrate A or A—(B)$_k$—(C)$_m$, wherein A, B, C, k and m are as defined for formula I and wherein all OH groups are protected, with the exception of the chlorine- or bromine-substituted 1—OH group, in the temperature range from −30° C. to +60° C., preferably from −5° C. to +30° C., with the exclusion of light. If a radical A—(B)$_k$—(C)$_m$ is to be added in the 5-position, then the desired carbohydrate may be bonded stepwise to a 13β-alkylmilbemycin, or said carbohydrate, preferably as a preformed glycoside, may be bonded to the 13β-alkylmilbemycin in one reaction step.

Suitable silver salts are freshly precipitated Ag$_2$O or, preferably, Ag$_2$CO$_3$ or CF$_3$—COOAg. A particularly preferred silver salt is silver trifluoromethanesulfonate (silver triflate=CF$_3$—SO$_3$Ag), in the presence of which the glycosidation takes place quickly even at temperatures below 0° C. In order to activate the 5—OH group of the 13β-alkylmilbemycin and to neutralise any CF$_3$—CO$_3$H or CF$_3$—COOH forming, it is convenient to add a tertiary amine (e.g. triethylamine, diisopropylethylamine, diazabicycloundecane etc.) to the reaction solution.

If desired, the protecting groups can subsequently be removed by mild saponification (e.g. NH$_3$/CH$_3$OH). Suitable solvents for this partial step are in particular anhydrous aprotic solvents such as dichloromethane, acetonitrile, benzene, toluene, nitromethane, dioxane, tetrahydrofuran, ethylene glycol dimethyl ether; diethyl ether is particularly suitable.

The protected 1-chloro- or 1-bromocarbohydrate is employed in equimolar amount, based on the 13β-alkylmilbemycin of formula I. However, it is preferably employed in excess, i.e. 1.5 to 3 times the equimolar amount. In order to obtain a satisfactory yield, the duration of the reaction is from 5 to 72 hours.

In place of the silver salt, mercuric cyanide or a combination of mercuric oxide with either mercuric chloride or mercuric bromide may also be employed (Helferich synthesis).

In accordance with a further variant, the reactivity in the 1'-position of the carbohydrate to be bonded glycosidically, the further OH groups of which must be protected, can be increased by initially converting said carbohydrate into the 1'-phenylthio derivative and subsequently reacting this derivative with DAST (=diethylaminosulfur trifluoride) in absolutely dry dichloromethane (e.g. in the presence of molecular sieve) at a temperature in the range from +5° C. to −30° C. to give the 1'-fluorine derivative. Compound with the corresponding 1'-chlorine or 1'-bromone derivative employed in Koenigs-Knorr synthesis, said 1'-fluorine derivative of the carbohydrate reactant can be bonded more reactively with a 13β-alkylmilbemycin of formula I, in the presence of $SnCl_2$ and $AgClO_4$, in a dry aprotic solvent such as diethyl ether, in an inert gas atmosphere (e.g. argon) and at a temperature in the range from +5° C. to −30° C. (q.v. J.Am.Soc. 1984, 106, pp. 4189–4192).

(B) A better reaction is obtained if the protected carbohydrate to be activated in the 1'-position is converted, at about 0° C. and in an argon atmosphere, with 2,2-dithiopyridine in dry dichloromethane into the 1'-S-(2-pyridyl)carbohydrate which readily reacts with the free 5—OH group of the 13β-alkylmilbemycin, in the presence of $Pb(ClO_4)_2$ or $AgClO_4$ as condensing agent, at room temperature and in tetrahydrofuran as solvent, to form the glycosidic bond (q.v. J. Org. Chem. 1983, 48, pp. 3489–3493).

(C) Glycosidic bonds can also be formed in the presence of Lewis acids such as $AlCl_3$, $AlBr_3$, $SnCl_4$, $ZnCl_2$, $BF_3$ (and, in particular, the etherate thereof), with acetylated sugars being particularly suitable for this type of bonding (q.v. Chimia 21, 1967, pp. 537–538).

(D) In accordance with the orthoester method, glycosidic bonds can also be formed by reacting the 13β-alkylmilbemycin with the sugar to be bonded, the OH groups of which sugar are protected, in the presence of the orthoester of a lower alcohol, one alcoholic component of which is the sugar reactant.

The process for the preparation of 13β-alkylmilbemycin derivatives, in the formula of which $R_1$, $R_2$, A, B, C, k and m are as defined for formula I, comprises, in the narrower sense, reacting a 13β-alkyl-5-hydroxymilbemycin of formula I (a) with the carbohydrate A or A—(B)$_k$—(C)$_m$ to be introduced, wherein A, B, C, k and m are as defined for formula I and wherein all OH groups are protected, with the exception of the anomeric 1—OH group substituted in the 1-position by chlorine or bromine, in the presence of a silver salt or mercury salt as condensing agent, with the exclusion of light and in the temperature range from −30° C. to +60° C., preferably from −5° C. to +30° C.; or (b) with the carbohydrate A or A—(B)$_k$—(C)$_m$ to be introduced, wherein all OH groups are protected, with the exception of the anomeric 1—OH group substituted in the 1-position by fluorine, in the presence of $SnCl_2$ and $AgClO_4$ as condensing agents, with the exclusion of light and in the temperature range from +5° C. to −30° C.; and, if desired, mildly saponifying the hydroxy protecting groups.

The trialkylaluminium compounds of formula III are generally known or can be prepared by methods analogous to those for the preparation of known representatives.

The starting esters of formula II can be prepared from the corresponding allyl alcohols of formula IV

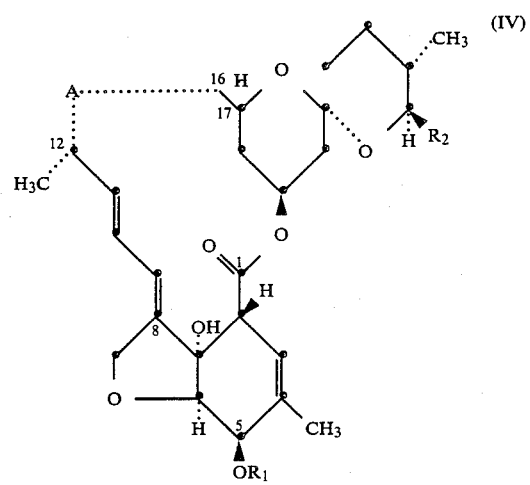

wherein A is one of the groups a or b

<pre>
                    CH3                         (a)
                    |
        HO          C
           ◂   ╱       ╲   ╱
            13          15
           CH          CH
            |
</pre>

[= 13β-hydroxy-Δ$^{14,15}$]

or

<pre>
                    CH3                         (b)
                    |
                    C
        13    ╱╱       ╲    15
        CH              CH  ╱
         |               ╲
                          OH
</pre>

[= Δ$^{13,14}$-15-hydroxy]

$R_2$ is as defined for formula I and $R_1$ is hydrogen or a silyl group indicated in the definition of formula I; by customary methods of acylation known in the literature, e.g. by reaction with an acid chloride ($R_8COCl$) or acid anhydride ($R_8CO)_2O$, wherein $R_8$ is as defined for formula I, in the presence of a base (triethylamine, pyridine, N,N-dimethylaminopyridine etc.), in an inert solvent such as mentioned above, e.g. dichloromethane, chloroform etc., and in the temperature range from −20° C. to 100° C., preferably from 0° C. to 70° C.

The compounds of formula IVb[=Δ$^{13,14}$-15-hydroxy] can be obtained by reacting 14,15-epoxymilbemycins of formula V

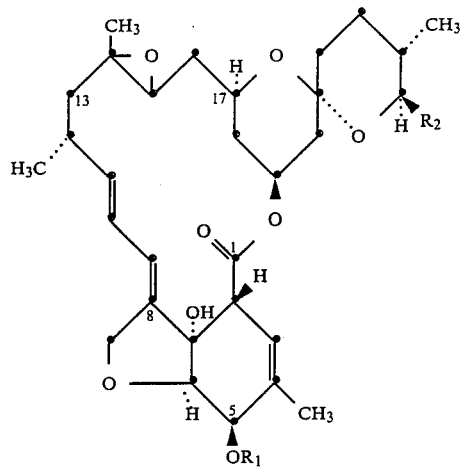

(V)

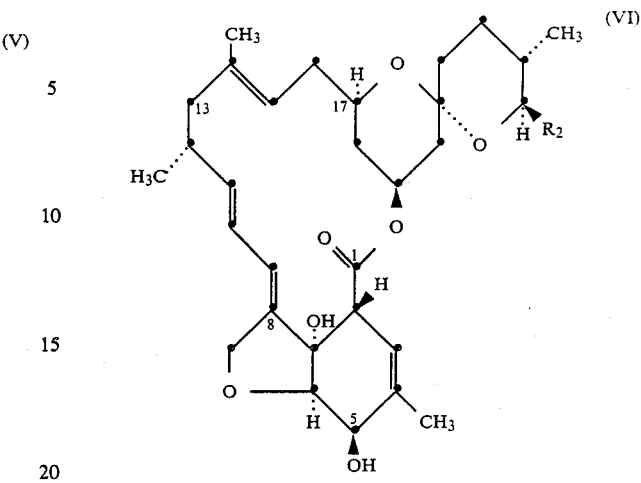

(VI)

wherein $R_1$ and $R_2$ are as defined for formula I, with the complex reagent $[HN_3]_m/[Al(ethyl)_3]_n$, wherein m and n are each independently 1 or 2 or a value between 1 and 2, in an inert dry solvent and in the temperature range from $-20°$ to $+150°$ C., preferably from $+20°$ to $+80°$ C.

Preferred inert solvents are aliphatic and aromatic hydrocarbons such as benzene, toluene, xylene, and petroleum ether; ethers such as diethyl ether, tert-butyl methyl ether, tetrahydrofuran, dioxane, and anisole.

The reaction is conveniently carried out in an inert gas such as nitrogen or argon.

Hydrazoic acid ($HN_3$) can also be converted, in the nascent state, into the $[HN_3]_m/[Al(Et)_3]_n$ complex by suspending sodium azide in the stipulated dry solvent or mixture of solvents and generating $HN_3$ in the solution with a stronger acid, e.g. $H_2SO_4$ (preferably oleum in order to ensure absolutely dry reaction conditions). $Al(Et)_3$ should already be present in the solution or added thereto shortly afterwards. The epoxy compound to be reacted can also already be present in the solution or added thereto at a suitable time.

The starting compounds of formula V, which are employed for the preparation of compounds of formula IVb, can be easily prepared by epoxidation of the compounds known from U.S. Pat. No. 3,950,360 and originally designated as "Antibiotics B-41-A", later called "milbemycin A" compounds, and of the compounds known from U.S. Pat. No. 4,346,171 and designated as "B-41-D" or "milbemycin D"; as well as of the 13-deoxy-22,23-dihydroavermectins ($R_2$=sec-butyl) of the formula VI $R_2 = CH_3$: milbemycin $A_3$
$R_2 = C_2H_5$: milbemycin $A_4$
$R_2 = isoC_3H_7$: milbemycin D
$R_2 = sec-C_4H_9$: 13-deoxy-22,23-dihydro-C-076-Bla-aglycon, known from U.S. Pat. No. 4,173,571.

The epoxidation is carried out in a solvent phase in the temperature range from $-10°$ to $+20°$ C., preferably from $-5°$ to $+5°$ C.

Peracids such as peracetic acid, trifluoroperacetic acid, perbenzoic acid and chloroperbenzoic acid are suitable for the epoxidation.

The $13\beta$-hydroxy-$\Delta^{14,15}$ compounds of formula IVa can be prepared by reacting compounds of formula IIb, wherein $R_1$ is a protecting group, with pyridinium dichromate [$=(Pyr)_2Cr_2O_7$]. This reaction is carried out in dimethylformamide and in the temperature range from $-10°$ to $+60°$ C. If desired, the protecting group $R_1$ is subsequently removed by hydrolysis.

By acylating or silylating the 5—OH group, all those derivatives of formulae I to VI are prepared wherein $R_1$ has a meaning other than hydrogen ($R_1$=OH protecting group). For the silylation it is convenient to use a silane of the formula $Y-Si(R_5)(R_6)(R_7)$, wherein each of $R_5$, $R_6$ and $R_7$ is one of the radicals indicated above and Y is a silyl leaving group. Examples of silyl leaving groups Y are bromide, chloride, cyanide, azide, acetamide, trifluoroacetate or trifluoromethanesulfonate. This recitation constitutes no limitation; further typical silyl leaving groups are known to the skilled person.

5-O-silylations are carried out in anhydrous medium, preferably in inert solvents and, most preferably, in aprotic solvents. The reaction conveniently takes place in the temperature range from 0° to $+80°$ C., preferably from $+10°$ to $+40°$ C. It is preferred to add an organic base. Examples of suitable bases are tertiary amines such as triethylamine, triethylenediamine, triazole and, preferably, pyridine, imidazole or 1,8-diazabicyclo[5.4.0]-undec-7-ene (DBU).

The removal of these silyl radicals $R_1$ in the 5-position is effected by selective mild hydrolysis ($\rightarrow$R=H) with e.g. arylsulfonic acid in alcoholic solution or in accordance with another method known to the skilled person.

The described process for the preparation of compounds of formula I constitutes in all its partial steps an object of the present invention.

The present invention also relates to pesticidal compositions for controlling ecto- and endoparasites as well as harmful insects, which compositions contain as active ingredient at least one compound of formula I, together with customary carriers and/or dispersing agents.

The compounds of formula I are most suitable for controlling pests of animals and plants, including ectoparasites of animals. These last mentioned pests comprise those of the order Acarina, in particular pests of the families Ixodidae, Dermanyssidae, Sarcoptidae, Psoroptidae; of the orders Mallophaga, Siphonaptera, Anoplura (e.g. family of the Haematopinidae); and of the order Diptera, in particular pests of the families Muscidae, Calliphoridae, Oestridae, Tabanidae, Hippoboscidae, and Gastrophilidae.

The compounds of formula I can also be used against hygiene pests, especially of the order Diptera (families Sarcophagidae, Anophilidae and Culicidae); of the order Orthoptera, of the order Dictyoptera (e.g. family of the Blattidae), and of the order Hymenoptera (e.g. family of the Formicidae).

The compounds of formula I also have a lasting action against mites and insects which are parasites of plants. When used to control spider mites of the order Acarina, they are effective against eggs, nymphs and adults of Tetranychidae (Tetranychus spp. and Panonychus spp.) They also have excellent activity against sucking insects of the order Homoptera, in particular against pests of the families Aphididae, Delphacidae, Cicadellidae, Psyllidae, Coccidae, Diaspididae and Eriophyidae (e.g. the rust mite on citrus fruit); of the orders Hemiptera, Heteroptera and Thysanoptera; and against plant-feeding insects of the orders Lepidoptera, Coleoptera, Diptera and Orthoptera.

The compounds of formula I are also suitable for use against soil pests.

The compounds of formula I are therefore effective against all development stages of sucking and feeding insects in crops such as cereals, cotton, rice, maize, soybeans, potatoes, vegetables, fruit, tobacco, hops, citrus fruit, avocados and others.

The compounds of formula I are also effective against plant nematodes of the species Meloidogyne, Heterodera, Pratylenchus, Ditylenchus, Radolphus, Rhizoglyphus and others.

Furthermore, the compounds of formula I act against helminths, among which the endoparasitic nematodes can be the cause of severe diseases in mammals and fowl, for example in sheep, pigs, goats, cattle, horses, donkeys, dogs, cats, guinea pigs, cage-birds. Typical nematodes having this indication are: Haemonchus, Trichostrongylus, Ostertagia, Nematodirus, Cooperia, Ascaris, Bunostomum, Oesphagostomum, Charbertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. The particular advantage of the compounds of formula I is their activity against those parasites which are resistant to benzimidazole-based parasiticides.

Certain species of the genera Nematodirus, Cooperia and Oesophagostomum attack the intestinal tract of the host animal, whereas others of the species Haemonchus and Ostertagia parasiticise in the stomach and those of the species Dictyocaulus in the lung tissue. Parasites of the families Filariidae and Setariidae are found in internal cell tissue and internal organs, e.g. in the heart, blood vessels, lymph vessels and in subcutaneous tissue. In this connection, particular mention is to be made of the dog heartworm, *Dirofilaria immitis*. The compounds of formula I are highly effective against these parasites.

The compounds of formula I are also suitable for controlling pathogenic parasites in humans, among which parasites there may be mentioned as typical representatives occurring in the alimentary tract those of the species Ancylostoma, Necator, Ascaris, Strongyloides, Trichinella, Capillaria, Trichuris and Enterobius. The compounds of this invention are also effective against parasites of the species Wuchereria, Brugia, Onchocerca and Loa of the family of the Filariidae which occur in the blood, in tissue and various organs, and, in addition, against Dracunculus and parasites of the species Strongyloides and Trichinella which infest in particular the gastro-intestinal tract.

The compounds of formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The compounds of formula I are administered to warm-blooded animals at rates of application of 0.01 to 10 mg/kg of body weight, and are applied to enclosed crop areas, to pens, livestock buildings or other buildings in amounts of 10 g to 1000 g per hectare.

The formulations, i.e. the compositions, preparations or mixtures containing the compound of formula I (active ingredient) are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the active ingredient to be formulated, suitable surface-active compounds are nonionic, cationic and/or anionic surfactants having good emulsifying, dispersing and wetting properties.

The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholiphids.

The surfactants customarily employed in the art of formulation are described e.g. in "McCutcheon's Detergents and Emulsifiers Annual", MC Publishing Corp. Ridgewood, N.J., 1982.

The pesticidal compositions usually contain 0.01 to 95%, preferably 0.1 to 80%, of a compound of formula I, 5 to 99.99% of a solid or liquid adjuvant, and 0 to 25%, preferably 0.1 to 25%, of a surfactant.

Whereas commercial products are preferably formulated as concentrates, the end user will normally employ dilute formulations having a concentration of 1–10,000 ppm.

The present invention therefore also relates to pesticidal compositions which contain as active ingredient at least one compound of formula I, together with customary carriers and/or dispersing agents.

The compositions may also contain further ingredients such as stabilisers, antifoams, viscosity regulators, binders, tackifiers as well as fertilisers or other active ingredients for obtaining special effects.

Preparatory Examples

Preparation of starting materials and intermediates

Example S1: Preparation of 14,15-epoxymilbemycin D (formula V)

While cooling with ice, a solution of 170 mg of chloroperbenzoic acid in 5 ml of dichloromethane is added to a solution of 550 mg of milbemycin D in 5 ml of dichloromethane. After stirring for 1 hour at 0° to 5° C., another 170 mg of the oxidising agent are added and stirring is continued for 30 minutes. When the reaction is complete, the solution is poured into an ice-cooled solution of sodium sulfite and extracted with ethyl acetate. The combined extracts are washed once with water, dried, and concentrated by evaporation in vacuo. The crude product is purified by chromatography through a column of silica gel (elution with a 20:15 mixture of n-hexane and ethyl acetate), affording 450 mg of amorphous, white 14,15-epoxymilbemycin D.

Example S2: Preparation of 15-hydroxy-$\Delta^{13,14}$-milbemycin D (formula IVb)

9.5 ml (0.41 g; 9.53 mmol) of a 6.96% solution of $HN_3$ in diethyl ether are added at $-20°$ C. to a solution of 2.1 ml (1.75 g; 15.3 mmol) of triethylaluminium in 8.5 ml of absolute diethyl ether. The reaction mixture is then added at $-10°$ C. to 1.8 g (3.15 mmol) of 14,15-epoxymilbemycin D (in substance). The ensuing reaction is strongly exothermic. After 1 hour at room temperature, 4 ml of absolute ether are added and the gelatinous reaction mixture is vigorously stirred. After 4 hours, the reaction mixture is worked up as described in Example S1. Chromatography through 70 g of silica gel (elution with a 10:1 mixture of $CH_2Cl_2$ and acetone) affords 200 mg (10%) of 14-azido-15-hydroxymilbemycin D and 820 mg (45%) of 15-hydroxy-$\Delta^{13,14}$-milbemycin D; m.p. 151°–153° C. (recrystallisation from methanol).

Example S3: Preparation of 5-O-tert-butyldimethylsilyl-14,15-epoxymilbemycin D (formula V)

A solution of 2.21 g (3.86 mmol) of 14,15-epoxymilbemycin D, 757 mg (5.02 mmol) of tert-butyldimethylchlorosilane and 342 mg (5.02 mmol) of imidazole in 4 ml of dimethylformamide is stirred for 90 minutes at room temperature. Then 80 ml of diethyl ether are added and the mixture is filtered through 20 g of silica gel and the filtrate is concentrated, affording 2.65 g (100%) of 5-O-tert-butyldimethylsilyl-14,15-epoxymilbemycin D.

$^1$H-NMR (300 MHz., solvent $CDCl_3$., $\delta$ values based on $Si(CH_3)_4$=TMS). 0.12 ppm (s) $(CH_3)_2Si$—O—; 0.92 ppm (s) (t—$C_4H_9$)Si—O—; 1.23 ppm (broad s) ($C_{14}CH_3$, i.e. signal of the $CH_3$ group in the 14-position); 2.56 ppm (d; J=9 Hz) ($C_{15}H$, i.e. signal of the proton in the 15-position).

Following the same procedure, the corresponding 5-O-trimethylsilyl-14,15-epoxymilbemycin D (m.p. 92°–97° C.) can be prepared by reaction with trimethylsilyl trifluoromethanesulfonate.

Example S4: Preparation of 5-O-tert-butyldimethylsilyl-15-hydroxy-$\Delta^{13,14}$-milbemycin D (formula IVb)

A solution of the $HN_3/Et_3Al$ complex reagent (prepared from a solution of 4.97 ml of triethyl aluminium in 7 ml of absolute tetrahydrofuran and 9.15 ml of a 2.39 molar solution of $HN_3$ (21.9 mmol) in absolute diethyl ether) is added, under argon, to a solution of 5.0 g (7.29 mmol) of 5-O-tert-butyldimethylsilyl-14,15-epoxymilbemycin D in about 20 ml of absolute tetrahydrofuran, and the mixture is heated under reflux for 15 hours. Then 250 ml of ether, 2 ml of methanol, and finally a mixture of 10 g of $Na_2SO_4.10H_2O$ and 10 g of celite are added at room temperature. The mixture is filtered and the filtrate is concentrated and chromatography of the crude product through 160 g silica gel (elution with 0–30% of ethyl acetate in hexane) affords 2.37 g (47%)

of 5-O-tert-butyldimethylsilyl-15-hydroxy-$\Delta^{13,14}$-milbemycin D.

$^1$H-NMR (300 MHZ, CDCl$_3$): 1.59 ppm (d; J=1 Hz) (C$_{14}$CH$_3$); 4.06 ppm (dd; J$_1$=11 Hz; J$_2$=4 Hz) (C$_{15}$H); 5.15 ppm (d; J=8 Hz) (C$_{13}$H).

In addition, 109 mg (2%) of 13β-azido-5-O-tert-butyldimethylsilylmilbemycin D are obtained.

Example S5: Preparation of 14,15-epoxymilbemycin A$_4$ (R$_2$=C$_2$H$_5$) (formula V)

A solution of 2.43 g (14.08 mmol) of m-chloroperbenzoic acid in 70 ml of dichloromethane is added dropwise at room temperature to a solution of 5.7 g (10.5 mmol) of milbemycin A$_4$ in 140 ml of dichloromethane and 120 ml of a 0.5 molar solution of NaHCO$_3$. The mixture is vigorously stirred for 1 hour at room temperature and then diluted with 300 ml of dichloromethane. The organic phase is washed with an aqueous solution of NaHCO$_3$, dried over Na$_2$SO$_4$ and concentrated, affording 5.7 g of epoxide as crude product.

Example S6: Preparation of 5-O-tert-butyldimethylsilyl-14,15-epoxy-milbemycin A$_4$ (formula V)

5.7 g of 14,15-epoxymilbemycin A$_4$ are dissolved in 10 ml of dry dimethylformamide. Then 0.63 g (9.16 mmol) of imidazole and 1.4 g (9.34 mmol) of tert-butyldimethylchlorosilane are added at room temperature. The mixture is stirred for 1 hour at room temperature and chromatographed through 150 g of silica gel (elution with a 4:1 mixture of hexane and ether), affording 2.84 g (40% of theory, based on milbemycin A$_4$) of the silylated epoxy derivative.

Example S7: Preparation of 5-O-tert-butyldimethylsilyl-15-hydroxy-$\Delta^{13,14}$-milbemycin A$_4$ (formula IVb)

The complex reagent HN$_3$/Al(ethyl)$_3$ is prepared as follows: To 2.8 ml (12.2 mmol) of Al(C$_2$H$_5$)$_3$ in 4 ml of absolute tetrahydrofuran are slowly added at about $-20°$ C., under argon, 5.28 ml (20.4 mmol) of an 10% solution of HN$_3$ in absolute diethyl ether. To this solution is added, under argon, a solution of 2.84 g (4.25 mmol) of the compound obtained in Example S6, and the mixture so obtained is heated for 4 hours under reflux. Then 500 ml of diethyl ether and 10 g of Na$_2$SO$_4$.10H$_2$O and 10 g of celite are added at room temperature. The mixture is filtered and the filtrate is concentrated. Chromatography of the crude product through 100 g of silica gel (elution with a 7:2 mixture of hexane and diethyl ether) affords 1.72 g (60% of theory) of the title compound.

$^1$H-NMR (300 MHz, CDCl$_3$; TMS): 1.59 ppm (broad s) (C$_{14}$CH$_3$); 4.05 ppm (broad s) (C$_{15}$H); 5.15 ppm (d; J=6 Hz) (C$_{13}$H). In addition, 0.1 g of 13β-azido-5-O-tert-butyldimethylsilylmilbemycin A$_4$ is obtained.

Example S8: Preparation of 15-hydroxy-$\Delta^{13,14}$-milbemycin A$_4$ (formula IVb)

Hydrolysis of 5 mg of the title compound of Example S7 with 1 ml of a 1% solution of p-toluenesulfonic acid in methanol and working up in diethyl ether with a 5% solution of sodium bicarbonate affords the title compound.

Example S9: Preparation of 14,15-epoxymilbemycin A$_3$ (R$_2$=CH$_3$) (formula V)

In accordance with the procedure described in Example S1, reaction of 220 mg of milbemycin A$_3$ in 5 ml of dichloromethane and 75 mg of chloroperbenzoic acid in 5 ml of dichloromethane at $-2°$ to $+5°$ C. over 1½ hours and purification through a column of silica gel affords 190 mg of 14,15-epoxymilbemycin A$_3$.

Example S10: Preparation of 5-O-tert-butyldimethylsilyl-14,15-epoxymilbemycin A$_3$ (formula V)

In accordance with the procedure of Example S3, reaction of 190 mg of 14,15-epoxymilbemycin A$_3$ and 120 mg of tert-butyldimethylchlorosilane in the presence of imidazole affords 217 mg of the title compound.

Example S11: Preparation of 5-O-tert-butyldimethylsilyl-15-hydroxy-$\Delta^{13,14}$-milbemycin A$_3$ (formula IVb)

In accordance with the epoxy cleavage of Example S7, 203 mg of the title compound are obtained from 210 mg of 5-O-tert-butyldimethylsilyl-14,15-epoxymilbemycin A$_3$, in absolute diethyl ether using the complex reagent HN$_3$/Et$_3$Al under argon, and subsequent purification.

$^1$H—NMR (300 MHz, CDCl$_3$; TMS): 1.58 ppm (broad s) (C$_{14}$CH$_3$); 4.05 ppm (broad s) (C$_{15}$H); 5.15 ppm (d; J=6 Hz) (C$_{13}$H).

Example S12: Preparation of 15-hydroxy-$\Delta^{13,14}$-milbemycin A$_3$ (formula IVb)

In accordance with the procedure described in Example S1, the reagent HN$_3$/Al(C$_2$H$_5$)$_3$ is freshly prepared and added dropwise at $-10°$ C. to a solution of 830 mg (3.05 mmol) of 14,15-epoxy-milbemycin A$_3$ in 7 ml of dry diethyl ether. After working up, 385 mg of 15-hydroxy-$\Delta^{13,14}$-milbemycin A$_3$ and 92 mg of 14-azido-15-hydroxy-milbemycin A$_3$ are obtained.

Example S13: Preparation of 13-deoxy-14,15-epoxy-22,23-dihydroavermectin-Bla-aglycon (R$_2$=sec-C$_4$H$_9$) (formula V)

In accordance with the procedure described in Example S5, 510 mg of the title compound are obtained from 520 mg of 13-deoxy-22,23-dihydroavermectin-Bla-aglycon [Tetrahedron Letters, Vol. 24, No. 48, pp. 5333–5336 (1983)] and 210 mg of m-chloroperbenzoic acid in 20 ml of dichloromethane.

Example S14: Preparation of 5-O-tert-butyldimethylsilyl-13-deoxy-14,15-epoxy-22,23-dihydroavermectin-Bla-aglycon (formula V)

In accordance with the procedure described in Example S6, 108 mg of the title compound are obtained from 220 mg of the title compound of Example S13 and 55 mg of tert-butyldimethyldichlorosilane in the presence of 25 mg of imidazole in 5 ml of dry dimethylformamide.

Example S15: Preparation of 13-deoxy-15-hydroxy-$\Delta^{13,14}$-22,23-dihydroavermectin-Bla-aglycon (formula IVb)

In accordance with the procedure described in Example S2, 112 mg of the title compound are obtained by reacting 220 mg of the title compound of Example S14 with the complex reagent consisting of 320 mg of Al($C_2H_5$)$_3$ and 110 mg of a 6.96% solution of HN$_3$ in a total of 16 ml of dry diethyl ether. In addition, 61 mg of 13-deoxy-14-azido-15-hydroxy-22,23-dihydroavermectin-B1a-aglycon are obtained.

Example S16

(a) Preparation of 5-O-tert-butyldimethylsilyl-13β-hydroxymilbemycin D and 13β-hydroxymilbemycin D (formula IVa)

A solution comprising 286 mg (0.41 mmol) of 5-O-tert-butyldimethylsilyl-15-hydroxy-$\Delta^{13,14}$-milbemycin D and 209 mg (0.56 mmol) of pyridinium dichromate (PDC) in 3 ml of dimethylformamide (DMF) is stirred for 30 minutes at room temperature. 1 ml of isopropanol is subsequently added and the mixture is stirred for 5 minutes and then diluted with 50 ml of ether. After a further 10 minutes, the mixture is filtered through silica gel and the filtrate is concentrated. Chromatography of the crude product through 20 g of silica gel (elution with a 1:2 mixture of ether and hexane) affords 165 mg (57%) of 5-O-tert-butyldimethylsilyl-13β-hydroxymilbemycin D.

$^1$H—NMR (300 MHz; CDCl$_3$; TMS): 1.59 ppm (br.s) ($C_{14}CH_3$) 3.70 ppm (d; J=10 Hz) ($C_{13}H$).

105 mg (0.153 mmol) of the compound so obtained are stirred at room temperature in 1 ml of a 1% solution of p-toluenesulfonic acid in methanol for 1 hour. The mixture is diluted with 20 ml of ether, filtered through silica gel and the filtrate is concentrated. The residue is chromatographed through about 10 g of silica gel (elution with a 1:4 mixture of acetone and dichloromethane), affording 73 mg (83%) of 13β-hydroxymilbemycin D.

$^1$H—NMR (300 MHz; CDCl$_3$; TMS): 1.58 ppm (br.s) ($C_{14}CH_3$) 3.71 ppm (d; J=10 Hz) ($C_{13}H$).

(b) Preparation of 5-O-tert-butyldimethylsilyl-13β-hydroxymilbemycin A$_4$

By following a procedure analogous to that described in (a), but starting from 5-O-tert-butyldimethylsilyl-15-hydroxy-$\Delta^{13,14}$-milbemycin A$_4$, the title compound with the following physical data is obtained:

$^1$H—NMR (300 MHz; CDCl$_3$; TMS): 3.05 ppm (t; J=9 Hz) ($C_{25}H$) 3.71 ppm (dd; J=3 and 10 Hz) ($C_{13}H$) mass spectrum (FD) m/e: 672 (M$^+$; $C_{38}H_{60}O_8Si$).

Example S17

(a) Preparation of 5-O-tert-butyldimethylsilyl-13β-acetoxymilbemycin D

A solution of 200 mg (0.29 mmol) of 5-O-tert-butyldimethylsilyl-13β-hydroxymilbemycin D and 1 ml of pyridine in 2 ml of acetanhydride is stirred for 2 hours at room temperature. Working up in diethyl ether affords 212 mg of 5-O-tert-butyldimethylsilyl-13β-acetoxymilbemycin D in the form of an amorphous powder.

(b) Preparation of 5-O-tert-butyldimethylsilyl-13β-acetoxymilbemycin A$_4$

By following a procedure analogous to that described in (a), but starting from 5-O-tert-butyldimethylsilyl-13β-hydroxymilbemycin A$_4$, the title compound with the following physical data is obtained:

$^1$H—NMR (360 MHz; CDCl$_3$; TMS): 1.53 ppm (s) ($C_{14}CH_3$), 2.03 ppm (s) ($CH_3COO$), 4.94 ppm (d; J=10 Hz) ($C_{13}H$), mass spectrum (FD) m/e: 714 (M$^+$; $C_{40}H_{62}O_9Si$).

Example S18

(a) Preparation of 5-O-tert-butyldimethylsilyl-15-acetoxy-$\Delta^{13,14}$-milbemycin D A solution of 627 mg (0.914 mmol) of 5-O-tert-butyldimethylsilyl-15-hydroxy-$\Delta^{13,14}$-milbemycin D in 2 ml of acetanhydride and 2 ml of pyridine is stirred for ½ hour at room temperature. Working up in diethyl ether with 5% aqueous NaHCO$_3$ solution and then with 1M HCl and filtration through silica gel affords 624 mg (94%) of 5-O-tert-butyldimethylsilyl-15-acetoxy-$\Delta^{13,14}$-milbemycin D.

$^1$H—NMR (300 MHz; CDCl$_3$; TMS): 1.58 ppm (br. s) ($C_{14}CH_3$), 1.79 ppm (br. s) ($C_4CH_3$), 2.02 ppm (s) ($CH_3COO$), 5.12–5.26 ppm (m) ($C_{10}H$; $C_{13}H$; $C_{15}H$).

(b) Preparation of 5-O-tert-butyldimethylsilyl-15-acetoxy-$\Delta^{13,14}$-milbemycin A$_4$ By following the procedure described in (a), but starting from 5-O-tert-butyldimethylsilyl-15-hydroxy-$\Delta^{13,14}$-milbemycin A$_4$, the title compound with the following physical data is obtained:

$^1$H—NMR (250 MHz; CDCl$_3$; TMS): 1.59 ppm (s) ($C_{14}CH_3$), 2.03 ppm (s) ($CH_3COO$), 3.02 ppm (t; J=8 Hz) ($C_{25}H$), 3.88 ppm (d; J=6 Hz) ($C_6H$), mass spectrum m/e: 714 (M$^+$; $C_{40}H_{62}O_9Si$), 639, 579, 497, 472, 437, 413, 412, 394, 349.

(c) Preparation of 5-O-tert-butyldimethylsilyl-15-acetoxy-$\Delta^{13,14}$-milbemycin A$_4$ The title compound is prepared by following a procedure entirely analogous to that described in (a) and (b), but starting from 5-O-tert-butyldimethylsilyl-15-hydroxy-$\Delta^{13,14}$-milbemycin A$_3$.

Preparation of final products of formula I

Example P1: Preparation of 13β-methylmilbemycin D

Under argon and at 0° C., 1.2 ml of a 17% solution of trimethylaluminum in toluene are added dropwise with stirring to a solution of 203 mg (0.28 mmol) of 5-O-tert-butyldimethylsilyl-15-acetoxy-$\Delta^{13,14}$-milbemycin D in 2 ml of dichloromethane. The solution is stirred for 2 hours at room temperature, then 0.3 ml of methanol is added dropwise, and the mixure is diluted with diethyl ether and stirred in celite. Filtration through silica gel (elution with diethyl ether) affords 177 mg of 5-O-tert-butyldimethylsilyl-13β-methylmilbemycin D. A solution of this material in 0.5 ml of dichloromethane is stirred in 1 ml of a 40% aqueous solution of HF in acetonitrile (5:95) for 1 hour at room temperature. The mixture is worked up in diethyl ether and filtered through silica gel. HPLC (SiO$_2$; 0.5% methanol in dichloromethane; pressure 50 bar) of the crude product (154 mg) affords (57%) of 13β-methylmilbemycin D.

$^1$H—NMR (300 MHz; CDCl$_3$; TMS): 1.01 ppm (d, J=6.7 Hz) ($C_{13}CH_3$), 5.03 ppm (dd, J=10.5 and 4.6 Hz) ($C_{15}H$), mass spectrum m/e: 570 (M$^+$; $C_{34}H_{50}O_7$), 442, 292, 273, 262, 210, 209, 181, 163, 152, 151.

Example P2

(a) Preparation of 13β-ethylmilbemycin D and 15-ethyl-Δ$^{13,14}$-milbemycin D

Under argon and at 0° C., 0.75 ml (0.63 g; 5.5 mmol) of triethylaluminium is added dropwise with stirring to a solution of 340 mg (0.47 mmol) of 5-O-tert-butyldimethylsilyl-15-acetoxy-Δ$^{13,14}$-milbemycin D in 2 ml of dichloromethane. The solution is stirred for 1 hour at room temperature, and then diluted with diethyl ether. Celite/Na$_2$SO$_4$:10H$_2$O (1:1) is added and the resultant mixture is stirred for 1 hour. Filtration through silica gel (elution with diethyl ether) affords 258 mg of a mixture which is dissolved in 0.5 ml of dichloromethane. This solution is then stirred in 1 ml of a 4% aqueous solution of HF in acetonitrile (5:95) for 1 hour at room temperature. Working up in diethyl ether, filtration through silica gel (elution with diethyl ether) and HPLC (reversed phase: water/methanol 1:9; pressure 50 mbar) of the crude product (183 mg) affords 88 mg (32%) of 13β-ethylmilbemycin D.

$^1$H-NMR (300 MHz; CDCl$_3$; TMS): 0.73 ppm (t, J=7.2 Hz) (C$_{13}$CH$_2$CH$_3$), 5.03 ppm (dd; J=10.5 und 4.4 Hz) (C$_{15}$H), mass spectrum m/e: 584 (M$^+$; C$_{35}$H$_{52}$O$_7$), 456, 287, 276, 210, 209, 181, 163, 151.

and 57 mg (21%) of 15-ethyl-Δ$^{13,14}$-milbemycin D.

$^1$H—NMR (300 MHz; CDCl$_3$; TMS): 3.03 ppm (m) (C$_{12}$H), 4.93 ppm (dd; J=8.7 and 1.2 Hz) (C$_{13}$H), mass spectrum m/e: 584 (M$^+$; C$_{35}$H$_{52}$O$_7$), 456, 438, 277, 276, 206, 181, 171, 163, 151, 150, 149.

By following procedures analogous to that of P2a, the following milbemycins of formula I indicated in P2b to P2h are obtained by reaction with the corresponding trialkyl compounds:

(P2b) 13β-Methylmilbemycin A$_4$
$^1$H—NMR (250 MHz; CDCl$_3$; TMS): 3.07 ppm (dt; J=12 and 10 Hz) (C$_{25}$H), 5.05 ppm (dd; J=10 and 5 Hz) (C$_{15}$H), mass spectrum (FD) m/e: 556 (M$^+$; C$_{33}$H$_{48}$O$_7$).

(P2c) 13β-Ethylmilbemycin A$_4$
$^1$H—NMR (250 MHz; CDCl$_3$; TMS): 3.03 ppm (broad t; J=10 Hz) (C$_{25}$H), 5.02 ppm (dd; J=10 and 7 Hz) (C$_{15}$H), mass spectrum (FD) m/e: 570 (M$^+$; C$_{34}$H$_{50}$O$_7$).

(P2d) 13β-n-Hexylmilbemycin D
$^1$H—NMR (250 MHz; CDCl$_3$; TMS): 3.08 ppm (d; J=8 Hz) (C$_{25}$H), 5.00 ppm (broad t; J=8 Hz) (C$_{15}$H), mass spectrum (FD) m/e: 640 (M$^+$; C$_{39}$H$_{60}$O$_7$).

(P2e) 13β-n-Butylmilbemycin A$_4$
$^1$H—NMR (250 MHz; CDCl$_3$; TMS); 3.03 ppm (broad t; J=10 Hz) (C$_{25}$H), 5.02 ppm (broad t; J=10 Hz) (C$_{15}$H), mass spectrum (FD) m/e: 598 (M$^+$; C$_{36}$H$_{54}$O$_7$).

(P2f) 13β-Isobutylmilbemycin A$_4$
$^1$H—NMR (250 MHz; CDCl$_3$; TMS): 3.09 ppm (broad t; J=10 Hz) (C$_{25}$H), 5.05 ppm (dd; J=10 and 7 Hz) (C$_{15}$H), mass spectrum (FD) m/e: 598 (M$^+$; C$_{36}$H$_{54}$O$_7$).

(H2g) 13β-Methylmilbemycin A$_3$
$^1$H—NMR (300 MHz; CDCl$_3$; TMS): 3.27 ppm (m) (C$_{25}$H), 5.06 ppm (dd; J=10 and 6 Hz) (C$_{15}$H), mass spectrum (FD) m/e: 542 (M$^+$; C$_{32}$H$_{46}$O$_7$).

(P2h) 13β-Ethylmilbemycin A$_3$
$^1$H—NMR (300 MHz; CDCl$_3$; TMS): 3.25 ppm (m) (C$_{25}$H), 5.06 ppm (dd; J=10 and 6 Hz) (C$_{15}$H), mass spectrum (FD) m/e: 556 (M$^+$; C$_{33}$H$_{48}$O$_7$)

Example P3: Preparation of 13β-methylmilbemycin D from 5-O-tert-butyldimethylsilyl-13β-acetoxymilbemycin D Under argon and at 0° C., 0.5 ml of a 17% solution of trimethylaluminium in toluene is added dropwise with stirring to a solution of 14 mg (0.019 mmol) of 5-O-tert-butyldimethylsilyl-13β-acetoxymilbemycin D in 0.5 ml of dichloromethane. The solution is stirred overnight at 5° C. Working up as indicated in P1 affords 10 mg of 5-O-tert-butyldimethylsilyl-13β-methylmilbemycin D.

A solution of this material in 0.5 ml of dichloromethane is stirred in 1 ml of a 40% aqueous solution of HF in acetonitirle (5:95) for 1 hour at room temperature. The mixture is worked up in diethyl and filtered through silica gel, affording 8 mg of 13β-methylmilbemycin D.

Example P4: Preparation of 13β-methyl-5-O-(2,3,4,6-tetra-O-acetyl-1-O-glucopyranosyl)milbemycin A$_4$ 185 mg (0.72 mmol) of silver triflate are added at room temperature to a solution of 49 mg (0.088 mmol) of 13β-methylmilbemycin A$_4$, 300 mg (0.72mmol) of 1-bromo-2,3,4,6-tetra-O-acetylglucose and 140 mg (1.1 mmol) of diisopropylethylamine in 30 ml of absolute diethyl ether. With the exclusion of light, the mixture is stirred for 15 hours, and the beige coloured precipitate is then isolated by filtration. The filtrate is diluted with 100 ml of diethyl ether, washed with two 15 ml portions of 1N NaHCO$_3$ solution and then with two 15 ml portions of water. After drying over Na$_2$SO$_4$, the solution is concentrated and purified through silica gel (elution with a 7:1 mixture of dichloromethane and diethyl ether). Freeze drying affords 74 mg (95% of theory) of a white amorphous powder.

$^1$H—NMR (250 MHz; CDCl$_3$; TMS): 3.10 ppm (broad t; J=10 Hz) (C$_{25}$H), 2.08 ppm (s) (4CH$_3$COO), mass spectrum (field desorption spectrum): m/e 886 (M$^+$ C$_{47}$H$_{66}$O$_{16}$)

Example P5: Preparation of 13β-methyl-5-O-tert-(2,3,4,6-tetra-O-acetyl-1-O-galactopyranosyl)milbemycin A$_4$ 185 mg (0.72 mmol) of silver triflate are added at room temperature to a solution of 50 mg (0.088 mmol) of 13β-methylmilbemycin A$_4$, 300 mg (0.72 mmol) of 1-bromo-2,3,4,6-tetra-O-acetylgalactose and 140 mg (1.1 mmol) of diisopropylamine in 50 ml of absolute diethyl ether. With the exclusion of light, the mixture is stirred for 20 hours, and the almost colourless precipitate is subsequently isolated by filtration. The filtrate is diluted with diethyl ether, washed with two 15 ml portions of 1N NaHCO$_3$ solution and then with two 15 ml portions of water. After drying over MgSO$_4$, the solution is concentrated and purified over silica gel (elution with a 7:1 mixture of dichloromethane and diethyl ether). Freeze drying affords 77 mg (95% of theory) of a white amorphous powder.

$^1$H—NMR (300 MHz; CDCl$_3$; TMS); 3.10 ppm (dt; J=2 and 10 Hz), 2.05 ppm (s) (3CH$_3$COO), 2.10 ppm (s) (1CH$_3$COO), mass spectrum (field desorption spectrum): m/e 886 (M$^+$; C$_{47}$H$_{66}$O$_{16}$)

The following compounds of formula I are prepared by procedures analogous to those described above. The following Table implies no limitations.

TABLE 1

Typical representatives of compounds of formula I, wherein $R_1$ is hydrogen

| Compound | $R_2$ | R |
|---|---|---|
| 1.1 | $CH_3$ | $CH_3$ |
| 1.2 | $CH_3$ | $C_2H_5$ |
| 1.3 | $CH_3$ | $C_3H_7$—n |
| 1.4 | $CH_3$ | $C_3H_7$—iso |
| 1.5 | $CH_3$ | $C_4H_9$—n |
| 1.6 | $CH_3$ | $C_4H_9$—sec |
| 1.7 | $CH_3$ | $C_4H_9$—iso |
| 1.8 | $CH_3$ | $C_5H_{11}$—n |
| 1.9 | $CH_3$ | $C_6H_{13}$—n |
| 1.10 | $CH_3$ | $C_7H_{15}$—n |
| 1.11 | $CH_3$ | $C_8H_{17}$—n |
| 1.12 | $CH_3$ | $C_9H_{18}$—n |
| 1.13 | $CH_3$ | $C_{10}H_{21}$—n |
| 1.14 | $C_2H_5$ | $CH_3$ |
| 1.15 | $C_2H_5$ | $C_2H_5$ |
| 1.16 | $C_2H_5$ | $C_3H_7$—iso |
| 1.17 | $C_2H_5$ | $C_4H_9$—n |
| 1.18 | $C_2H_5$ | $C_4H_9$—sec |
| 1.19 | $C_2H_5$ | $C_4H_9$iso |
| 1.20 | $C_2H_5$ | $C_5H_{11}$—n |
| 1.21 | $C_2H_5$ | $C_6H_{13}$—n |
| 1.22 | $C_3H_7$—iso | $CH_3$ |
| 1.23 | $C_3H_7$—iso | $C_2H_5$ |
| 1.24 | $C_3H_7$—iso | $C_3H_7$—n |
| 1.25 | $C_3H_7$—iso | $C_3H_7$—iso |
| 1.26 | $C_3H_7$—iso | $C_4H_9$—n |
| 1.27 | $C_3H_7$—iso | $C_4H_9$—sec |
| 1.28 | $C_3H_7$—iso | $C_4H_9$—iso |
| 1.29 | $C_4H_9$—sec | $CH_3$ |
| 1.30 | $C_4H_9$—sec | $C_2H_5$ |
| 1.31 | $C_4H_9$—sec | $C_3H_7$—n |
| 1.32 | $C_4H_9$—sec | $C_3H_7$—iso |
| 1.33 | $C_4H_9$—sec | $C_4H_9$—n |
| 1.34 | $C_4H_9$—sec | $C_4H_9$—sec |
| 1.35 | $C_4H_9$—sec | $C_4H_9$—tert |
| 1.36 | $C_4H_9$—sec | $C_4H_9$—iso |
| 1.37 | $C_3H_7$—iso | $C_6H_{13}$—n |
| 1.38 | $C_3H_7$—iso | $C_5H_{11}$—n |
| 1.39 | $C_2H_5$ | $C_3H_7$—n |

TABLE 2

Typical representatives of compounds of formula I, wherein $R_1$ is a silyl group

| Compound | $R_2$ | R | $R_1$ |
|---|---|---|---|
| 2.1 | $CH_3$ | $CH_3$ | tert-butyldimethylsilyl |
| 2.2 | $CH_3$ | $C_2H_5$ | tert-butyldimethylsilyl |
| 2.3 | $CH_3$ | $C_3H_7$—n | tert-butyldimethylsilyl |
| 2.4 | $CH_3$ | $C_3H_7$—iso | tert-butyldimethylsilyl |
| 2.5 | $CH_3$ | $C_4H_9$—n | tert-butyldimethylsilyl |
| 2.6 | $CH_3$ | $C_4H_9$—sec | tert-butyldimethylsilyl |
| 2.7 | $CH_3$ | $C_4H_9$—tert | tert-butyldimethylsilyl |
| 2.8 | $C_2H_5$ | $CH_3$ | tert-butyldimethylsilyl |
| 2.9 | $C_3H_7$ | $CH_3$ | tert-butyldimethylsilyl |
| 2.10 | $C_3H_7$—iso | $CH_3$ | tert-butyldimethylsilyl |
| 2.11 | $C_4H_9$—n | $CH_3$ | tert-butyldimethylsilyl |
| 2.12 | $C_4H_9$—sec | $CH_3$ | tert-butyldimethylsilyl |
| 2.13 | $C_4H_9$—iso | $CH_3$ | tert-butyldimethylsilyl |
| 2.14 | $CH_3$ | $CH_3$ | trimethylsilyl |
| 2.15 | $CH_3$ | $CH_3$ | tris(tert-butyl)silyl |
| 2.16 | $CH_3$ | $CH_3$ | diphenyl-tert-butylsilyl |
| 2.17 | $CH_3$ | $CH_3$ | bis(isopropyl)methylsilyl |
| 2.18 | $CH_3$ | $CH_3$ | triphenylsilyl |

TABLE 3

Typical representatives of compounds of formula I, wherein $R_1$ is the group

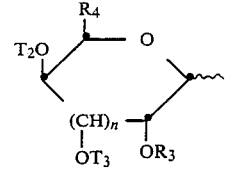

and $R_2$ and R are methyl (if $R_2$ and R have other meanings, this shall be specifically stated):

| Compound | $R_1$ | $R_2$ |
|---|---|---|
| 3.1 | $C_5$—D—ribose | |
| 3.2 | $C_5$—D—arabionose | |
| 3.3 | $C_5$—D—xylose | |
| 3.4 | $C_5$—D—lyxose | |
| 3.5 | $C_6$—D—allose | |
| 3.6 | $C_6$—D—altrose | |
| 3.7 | $C_6$—D—glucose | |

TABLE 3-continued

Typical representatives of compounds of formula I, wherein $R_1$ is the group

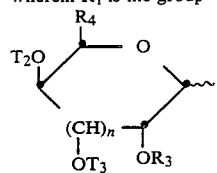

and $R_2$ and R are methyl (if $R_2$ and R have other meanings, this shall be specifically stated):

| Compound | $R_1$ | $R_2$ |
|---|---|---|
| 3.8 | $C_6$—D—mannose | |
| 3.9 | $C_6$—D—gulose | |
| 3.10 | $C_6$—D—idose | |
| 3.11 | $C_6$—D—galactose | |
| 3.12 | $C_6$—D—talose | |
| 3.13 | $C_5$—D—ribose | |
| 3.14 | $C_5$—D—arabinose | |

TABLE 3-continued

Typical representatives of compounds of formula I, wherein $R_1$ is the group

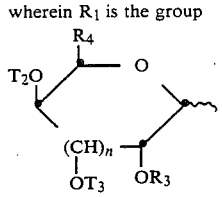

and $R_2$ and R are methyl (if $R_2$ and R have other meanings, this shall be specifically stated):

| Compound | $R_1$ | $R_2$ |
|---|---|---|
| 3.15 | $C_5$—D—xylose | |
| 3.16 | $C_5$—D—lyxose | |
| 3.17 | $C_6$—D—allose | |
| 3.18 | $C_6$—D—altrose | |
| 3.19 | $C_6$—D—glucose | |
| 3.20 | $C_6$—D—mannose | |

TABLE 3-continued

Typical representatives of compounds of formula I, wherein $R_1$ is the group $$\begin{array}{c} R_4 \\ T_2O \diagdown \diagup O \\ \mid \\ (CH)_n \\ \mid \quad \mid \\ OT_3 \quad OR_3 \end{array}$$

and $R_2$ and R are methyl (if $R_2$ and R have other meanings, this shall be specifically stated):

| Compound | $R_1$ | $R_2$ |
|---|---|---|
| 3.21 | $C_6$—D—gulose | |
| 3.22 | $C_6$—D—idose | |
| 3.23 | $C_6$—D—galactose | |
| 3.24 | $C_6$—D—talose | |
| 3.25 | $C_6$—D—psicose | |
| 3.26 | $C_6$—D—fructose | |
| 3.27 | $C_6$—D—sorbose | |
| 3.28 | $C_6$—D—tagatose | |
| 3.29 | 2,3,4,6-tetra-O—methyl-($C_6$—D—glucose) | |
| 3.30 | 2,3,4,6-tetra-O—acetyl-($C_6$—D—glucose) | $C_2H_5$ |
| 3.31 | 6-O—acetyl-($C_6$—D—glucose) | |
| 3.32 | 2,3,4,6-tetra-O—benzoyl-($C_6$—D—glucose) where U = benzoyl | |
| 3.33 | 2,3,4,5-tetra-O—acetyl-($C_6$—D—galactose) | $C_2H_5$ |

TABLE 3-continued

Typical representatives of compounds of formula I, wherein $R_1$ is the group

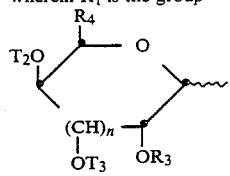

and $R_2$ and R are methyl (if $R_2$ and R have other meanings, this shall be specifically stated):

| Compound | $R_1$ | $R_2$ |
|---|---|---|
| 3.34 | CH₃OCOCH₂ — 6-O—acetyl-($C_6$—D—galactose) | |
| 3.35 | CH₃OCOCH₂ — 2,3,5-tri-O—acetyl-($C_5$—D—ribose) | |
| 3.36 | CH₃OCOCH₂ — 5-O—acetyl-($C_5$—D—ribose) | |
| 3.37 | 2,3,4-tri-O—acetyl-($C_5$—D—xylose) | |
| 3.38 | 2,3,4-tri-O—acetyl-($C_6$—D—rhamnose) where U = acetyl | |

Formulation Examples for active ingredients of formula I (throughout, percentages are by weight)

| Wettable powders | (a) | (b) | (c) |
|---|---|---|---|
| a compound of the Tables | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
|---|---|
| a compound of the Tables | 10% |
| octylphenol polyethylene glycol ether (4–5 moles of ethylene oxide) | 3% |
| calcium dodecylbenzenesulfonate | 3% |
| caster oil polygycol ether (36 moles of ethylene oxide) | 4% |
| cyclohexanone | 30% |
| xylene mixture | 50% |

Emulsions of any required concentration can be obtained from this concentrate by dilution with water.

| Dusts | (a) | (b) |
|---|---|---|
| a compound of the Tables | 5% | 8% |
| talcum | 95% | — |
| kaolin | — | 92% |

Ready for use dusts are obtained by mixing the active ingredient with the carrier, and grinding the mixture in a suitable mill.

| Extruder granulate | |
|---|---|
| a compound of the Tables | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| Tablets of boluses | | |
|---|---|---|
| I | a compound of the Tables | 33.00% |
| | methyl cellulose | 0.80% |
| | highly dispersed silicic acid | 0.80% |
| | maize starch | 8.40% |

The methyl cellulose is stirred in water and allowed to swell. Then the silicic acid is stirred in to give a homogeneous suspension. The compound of formula I and the maize starch are mixed and the aqueous suspension is added to the mix, which is kneaded to a paste. This paste is granulated through a 12M sieve and the granulate is dried.

| | | |
|---|---|---|
| II | crystalline lactose | 22.50% |
| | maize starch | 17.00% |
| | microcrystalline cellulose | 16.50% |
| | magnesium stearate | 1.00% |

All 4 adjuvants are thoroughly mixed. Phases I and II are mixed and compressed to tablets or boluses.

If the compounds of formula I, or compositions containing them, are used for controlling endoparasitic nematodes, cestodes and trematodes in domestic animals and productive livestock, for example cattle, sheep, goats, cats and dogs, they can be administered to the animals in both single and repeated doses. Depending on the species of animal, the individual doses are preferably administered in amounts ranging from 0.1 to 10 mg/kg of body weight. A better action is often achieved by protracted administration, or lower total doses will also suffice. The compounds, or compositions containing them, can also be added to feeds and drinks. The ready-prepared feeds contain the active ingredients preferably in a concentration of 0.005 to 0.1 percent by weight. The compositions can be administered to the animals perorally in the form of solutions, emulsions, suspensions, powders, tablets, boluses or capsules.

If the physical and toxicological properties of solutions or emulsions permit it, the compounds of formula I, or compositions containing them, can also be injected into animals for example subcutaneously, administered intraruminally or applied to the bodies of the animals by the pour-on method. Administration by means of salt licks or molasses blocks is also possible.

Biological Examples

B1: Insecticidal stomach poison action against *Spodoptera littoralis*

Potted cotton plants in the 5-leaf stage are sprayed with a solution containing 3, 12.5 or 50 ppm of the test compound in acetone/water. After the coating has dried, the plants are populated with about 30 larvae ($L_1$ stage) of *Spodoptera littoralis*. Two plants are used for each test compound and test species. The test is carried out at about 24° C. and 60% relative humidity. Evaluations and intermediate evaluations of moribund insects, larval growth and feeding damage are made after 24, 48 and 72 hours. Complete kill was achieved after 24 hours with the compounds of formula I of the Tables, e.g. compounds 1.14, 1,17, 1.22 and 1.23, at a concentration of 3 ppm.

B2: Action against plant-destructive acarids: OP-sensitive *Tetranychus urticae*

16 hours before the start of the test, the primary leaves of bean plants (*Phaseolus vulgaris*) are infected with an infested piece of leaf from a mass culture of *Tetranychus urticae*. Upon removal of the piece of leaf, the plants infested with all stages of the mites are sprayed to drip point with a solution containing 0.4 ppm or 1.6 ppm of the test compound. The temperature in the greenhouse compartment is about 25° C.

The percentage of mobile stages (adults and nymphs) and of eggs is evaluated under a stereoscopic microscope after 7 days. Compounds of formula I of the Tables, e.g. compounds 1.22 and 1.23, achieved complete kill at a concentration of 0.4 ppm.

B3: Action against $L_1$ larvae of *Lucilia sericata*

1 ml of an aqueous suspension of test compound is mixed with 3 ml of a special larval culture medium at about 50° C. such that a homogeneous composition containing 250 ppm or 125 ppm is obtained. About 30 *Lucilia sericata* larvae ($L_1$) are put into each test tube containing active ingredient. A mortality count is made after 4 days. The compounds of formula I of the Tables, e.g. compounds 1.14, 1.15, 1.17, 1.22 and 1.23, achieved complete kill at 100 ppm.

B4: Acaricidal action against *Boophilus microplus* (Biarra strain)

Adhesive tape is applied vertically across a PVC plate so that 10 fully replete female *Boophilus microplus* ticks (Biarra strain) can be affixed thereto with their backs, side by side, in a row. Each tick is injected from an injection needle with 1 μl of a liquid which contains a 1:1 mixture of polyethylene glycol and acetone, in which mixture a specific amount of test compound of 1, 0.1 or 0.01 μg per tick is dissolved. Control ticks are injected with liquid containing no test compound. After this treatment, the ticks are detached from the support and kept in an insectarium under normal conditions at about 28° C. and 80% relative humidity until oviposition has taken place and the larvae have hatched from the eggs of the control ticks. The activity of the test compound is determined with the $IR_{90}$, i.e. the effective dose is determined at which 9 out of 10 female ticks (90%) even after 30 days lay eggs from which larvae are unable to hatch.

Compounds of formula I of the Tables, e.g. compounds 1.14, 1.15, 1.22 and 1.23, achieved an $IR_{90}$ of 0.1 μg.

B5: Trial with sheep infected with nematodes (*Haemonchus concortus* and *Trichostrongylus colubriformis*)

The test compound is administered in the form of a suspension with a stomach probe or by intraruminal injection to sheep which have been artificially infected with *Haemonchus concortus* and *Trichostrongylus colubriformis*. 1 to 3 animals are used for each dose. Each sheep is treated only once with a single dose of 0.5 mg or 0.2 mg/kg of body weight. Evaluation is made by comparing the number of worm eggs excreted in the faeces of the sheep before and after treatment.

Untreated sheep infected simultaneously and in the same manner are used as controls. In comparison with untreated and infected control groups, there is no nematode infestation (=complete reduction of the number of worm eggs in the faeces) in sheep which have been treated with one of the compounds of formula I, e.g. compound 1.14, 1.15, 1.17, 1.22, 1.23 or 3.30, at 0.2 mg/kg.

B6: Contact action against *Aphis craccivora*

Pea plantlets which have been infested with all development stages of the aphid are sprayed with a solution prepared from an emulsifiable concentrate of the test compound and containing 50 ppm, 25 ppm or 12.5 ppm of active ingredient. After 3 days evaluation is made to establish whether at least 80% of the aphids are dead or have dropped from the plants. A composition is only rated as effective at this level of activity.

Compounds of formula I of the Tables, e.g. compounds 1.14, 1.15, 1.17, 1.22, 1.23 and 3.30, achieved complete kill (=100%) at a concentration of 12.5 ppm.

B7: Larvicidal action against *Aëdes aegypti*

A 0.1% solution of the test compound in acetone is pipetted onto the surface of 150 ml of water in beakers in amounts sufficient to give concentrations of 10 ppm, 3.3 ppm and 1.6 ppm. After the acetone has evaporated, 30 to 40 three-day-old larvae of *Aëdes aegypti* are put into each beaker. Mortality counts are made after 1, 2 and 5 days.

In this test, the compounds of formula I of the Tables, e.g. compounds 1.14, 1.15, 1.22, 1.23 and 3.30, achieved complete kill of all larvae at a concentration of 1.6 ppm after 1 day.

What is claimed is:

1. A compound of formula I

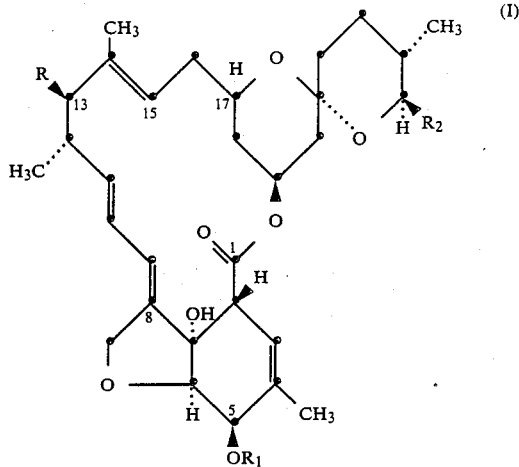

(I)

wherein
R is $C_1$–$C_{10}$alkyl;
$R_1$ is hydrogen, a silyl group or a mono-, di- or trisaccharide sugar residue in the furanosyl or pyranosyl form or in a form containing an amino radical, a thiol radical or a cyclic acetal radical; and
$R_2$ is methyl, ethyl, isopropyl or sec-butyl.

2. A compound of formula I according to claim 1, wherein R is $C_1$–$C_{10}$alkyl; $R_1$ is hydrogen, a silyl group or the residue —A—(B)$_k$—(C)$_m$, wherein A is a monosaccharide residue which is bonded in the 1'-position and which carries in the 2'-position either a hydroxy group or a readily removable group bonded through oxygen, and which residue A is bonded glycosidically to a second or third monosaccharide molecule B or C and each of k and m independently of the other is 0 or 1; and $R_2$ is methyl, ethyl, isopropyl or sec-butyl.

3. A compound of formula I according to claim 1, wherein R is $C_1$–$C_{10}$alkyl; $R_1$ is the group —Si($R_5$)($R_6$)($R_7$), wherein each of $R_5$, $R_6$ and $R_7$ independently of one another is $C_1$–$C_4$alkyl, benzyl or phenyl; and $R_2$ is methyl, ethyl, isopropyl or sec-butyl.

4. A compound of formula I according to claim 3, wherein R is $C_1$–$C_4$-alkyl; $R_1$ is trimethylsilyl, tris(tert-butyl)silyl, diphenyl-tert-butylsilyl, bis(isopropyl)methylsilyl, triphenylsilyl or tert-butyldimethylsilyl; and $R_2$ is methyl, ethyl, isopropyl or sec-butyl.

5. A compound of formula I according to claim 1, wherein R is $C_1$–$C_{10}$alkyl; $R_1$ is the sugar residue

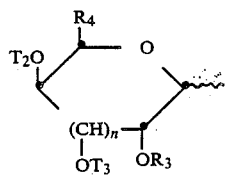

including the position isomers thereof, in which formula n is 0 or 1, $R_4$ is hydrogen, methyl or —CH$_2$—O—T$_1$, and each of $R_3$, $T_1$, $T_2$ $T_3$ independently of one another is hydrogen, methyl, benzyl an unsubstituted or halogenated $C_1$–$C_6$aliphatic acyl group, a benzoyl group, or a $C_1$–$C_6$alkoxycarbonyl group, or $T_1$ and $T_2$ together with the carbon atom of the carbonyl group of an aliphatic or aromatic aldehyde or ketone form a cyclic acetal containing not more than 13 carbon atoms; and $R_2$ is methyl, ethyl, isopropyl or sec-butyl.

6. A compound of formula I according to claim 5, wherein R is $C_1$–$C_4$alkyl; $R_3$ is methyl, benzyl, benzoyl, unsubstituted or fluorinated propionyl, acetyl, methoxycarbonyl or ethoxycarbonyl; and $R_2$, $R_4$, $T_2$ and $T_3$ are as defined in claim 5.

7. A compound of formula I according to claim 1, wherein R is $C_1$–$C_{10}$alkyl; $R_1$ is hydrogen; and $R_2$ is methyl, ethyl, isopropyl or sec-butyl.

8. A compound of formula I according to claim 7, wherein R is $C_1$–$C_6$alkyl; $R_1$ is hydrogen; and $R_2$ is methyl, ethyl, isopropyl or sec-butyl.

9. A compound of formula I according to claim 8, wherein R is $C_1$–$C_4$alkyl; $R_1$ is hydrogen; and $R_2$ is methyl, ethyl, isopropyl or sec-butyl.

10. A compound of formula I according to claim 9, wherein R is methyl, ethyl, n-propyl or isopropyl; $R_1$ is hydrogen; and $R_2$ is methyl, ethyl or isopropyl.

11. A compound of formula I according to claim 1, selected from the series consisting of:
13$\beta$-n-hexylmilbemycin D,
13$\beta$-methylmilbemycin D,
13$\beta$-ethylmilbemycin D,
13$\beta$-n-propylmilbemycin A$_4$,
13$\beta$-isopropylmilbemycin A$_4$,
13$\beta$-methylmilbemycin A$_3$,
13$\beta$-ethylmilbemycin A$_3$,
13$\beta$-methylmilbemycin A$_4$,
13$\beta$-ethylmilbemycin A$_4$,
13$\beta$-isobutylmilbemycin A$_4$,
13$\beta$-n-butylmilbemycin A$_4$.

12. A pesticidal composition comprising a pesticidally effective amount of a compound of claim 1 together with carriers or dispersing agents.

13. A pesticidal composition according to claim 12 wherein in the compound of formula I, R is $C_1$–$C_{10}$-alkyl; $R_1$ is hydrogen; and $R_2$ is methyl, ethyl, isopropyl or sec-butyl.

14. A method of combatting ecto- and endoparasites and harmful insects affecting animals, which process comprises treating the infested animal or the locus of the pest with a pesticidally effective amount of a compound of claim 1.

15. A method according to claim 14, wherein the pests to be controlled are ectoparasites, endoparasites and insects of animals.

16. A method according to claim 15, wherein the endoparasites are endoparasites in warm-blooded animals.

17. A method according to claim 16, wherein the endoparasites are nematodes.

18. A method of protecting plants from phytopathogenic pests, which process comprises treating the infested plant or the locus of the pest with a pesticidally effective amount of a compound of claim 1.

* * * * *